(12) United States Patent
Lee et al.

(10) Patent No.: US 9,421,305 B2
(45) Date of Patent: Aug. 23, 2016

(54) ALIGNED SCAFFOLDING SYSTEM FOR SKELETAL MUSCLE REGENERATION

(75) Inventors: Sang Jin Lee, Winston-Salem, NC (US); James J. Yoo, Winston-Salem, NC (US); Anthony Atala, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 1220 days.

(21) Appl. No.: 12/865,434

(22) PCT Filed: Jan. 30, 2009

(86) PCT No.: PCT/US2009/000625
§ 371 (c)(1),
(2), (4) Date: Aug. 11, 2010

(87) PCT Pub. No.: WO2009/099570
PCT Pub. Date: Aug. 13, 2009

(65) Prior Publication Data
US 2010/0331980 A1  Dec. 30, 2010

Related U.S. Application Data

(60) Provisional application No. 61/025,350, filed on Feb. 1, 2008.

(51) Int. Cl.
*A61F 2/08* (2006.01)
*A61L 27/48* (2006.01)
*A61L 27/26* (2006.01)
(Continued)

(52) U.S. Cl.
CPC ............... *A61L 27/48* (2013.01); *A61L 27/26* (2013.01); *A61L 27/3826* (2013.01); *A61L 27/3873* (2013.01); *A61L 27/58* (2013.01); *A61L 2430/30* (2013.01)

(58) Field of Classification Search
CPC .......................................................... A61F 2/08
USPC ................... 623/14.11–14.13; 424/93.7, 423
See application file for complete search history.

(56) References Cited

U.S. PATENT DOCUMENTS

| 6,171,344 | B1 | 1/2001 | Atala |
| 6,592,623 | B1 * | 7/2003 | Bowlin et al. ............. 623/14.13 |
| 2004/0037813 | A1 * | 2/2004 | Simpson et al. ............. 424/93.7 |

(Continued)

FOREIGN PATENT DOCUMENTS

| WO | WO 2006/099315 A2 | 9/2006 |
| WO | WO 2006/106506 A2 | 10/2006 |

OTHER PUBLICATIONS

Saxena AK et al. Skeletal muscle tissue engineering using isolated myoblasts on synthetic biodegradable polymers: preliminary studies. Tissue Engineering. 1999; 5(6): 525-531.

(Continued)

*Primary Examiner* — Suzette J Gherbi
(74) *Attorney, Agent, or Firm* — Myers Bigel & Sibley, P.A.

(57) ABSTRACT

Provided herein are anisotropic muscle implants that have a biodegradable scaffold comprising a plurality of fibers oriented along a longitudinal axis. The implants may include mammalian muscle cells seeded and/or fused into myotubes on the scaffold. Methods of forming the muscle implants are provided, as are methods of treating a subject in need of skeletal muscle reconstruction.

27 Claims, 10 Drawing Sheets

(51) Int. Cl.
*A61L 27/38* (2006.01)
*A61L 27/58* (2006.01)

(56) References Cited

U.S. PATENT DOCUMENTS

| | | | |
|---|---|---|---|
| 2005/0260706 A1 | 11/2005 | Kaplan et al. | |
| 2006/0198827 A1* | 9/2006 | Levenberg et al. | 424/93.7 |
| 2006/0257377 A1* | 11/2006 | Atala et al. | 424/93.7 |
| 2007/0269481 A1* | 11/2007 | Li et al. | 424/423 |
| 2009/0265005 A1* | 10/2009 | Yoo et al. | 623/14.13 |

OTHER PUBLICATIONS

Payumo FC et al. Tissue engineering skeletal muscle for orthopaedic applications. Clinical Orthopaedics & Related Research. Oct. 2002; 403: S228-S242.
Powell CA et al. Mechanical stimulation improves tissue-engineered human skeletal muscle. Am J Physiol Cell Physiol. 2002; 238: C1557-C1565.
Neumann T et al. Tissue engineering of skeletal muscle using polymer fiber arrays. Tissue Engineering. 2003; 9(5): 995-1003.
Bach AD et al. Skeletal muscle tissue engineering. J Cell Mol Med. 2004; 8(4): 413-422.
Kamelgar FS et al. A comparative study of three different biomaterials in the engineering of skeletal muscle using a rat animal model. Biomaterials. 2004; 25: 1649-1655.
Li D and Xia Y. Electrospinning of nanofibers: reinventing the wheel? Advanced Materials. Jul. 19, 2004; 16(14): 1151-1170.
Levenberg S et al. Engineering vascularized skeletal muscle tissue. Nature Biotechnology. Jul. 2005; 23(7): 879-884.
Riboldi SA et al. Electrospun degradable polyesterurethane membranes: potential scaffolds for skeletal muscle tissue engineering. Biomaterials. 2005; 26: 4606-4615.
Courtney T et al. Design and analysis of tissue engineering scaffolds that mimic soft tissue mechanical anisotropy. Biomaterials. 2006; 27: 3631-3638.
Stankus JJ et al. Microintegrating smooth muscle cells into a biodegradable, elastomeric fiber matrix. Biomaterials. 2006; 27: 735-744.
Stitzel J et al. Controlled fabrication of a biological vascular substitute. Biomaterials. 2006; 27: 1088-1094.
Lee SJ et al. In vitro evaluation of electrospun nanofiber scaffolds for vascular graft application. Journal of Biomedical Materials Research Part A. 2007; 83A: 999-1008.
Liang D et al. Functional electrospun nanofibrous scaffolds for biomedical applications. Advanced Drug Delivery Reviews. 2007; 59: 1392-1412.
Choi JS et al. The influence of electrospun aligned poly(ϵ-caprolactone)/collagen nanofiber meshes on the formation of self-aligned skeletal muscle myotubes. Biomaterials. 2008; 29: 2899-2906.
Lee SJ et al. Development of composite vascular scaffolding system that withstands physiological vascular conditions. Biomaterials. 2008; 29: 2891-2898.
Corning Life Sciences. Reducing serum levels and culture costs. Corning Incorporated, Acton, MA. Undated: 4 pp.
International Search Report and Written Opinion, PCT/US2009/000625, mailed Jun. 16, 2010.

* cited by examiner

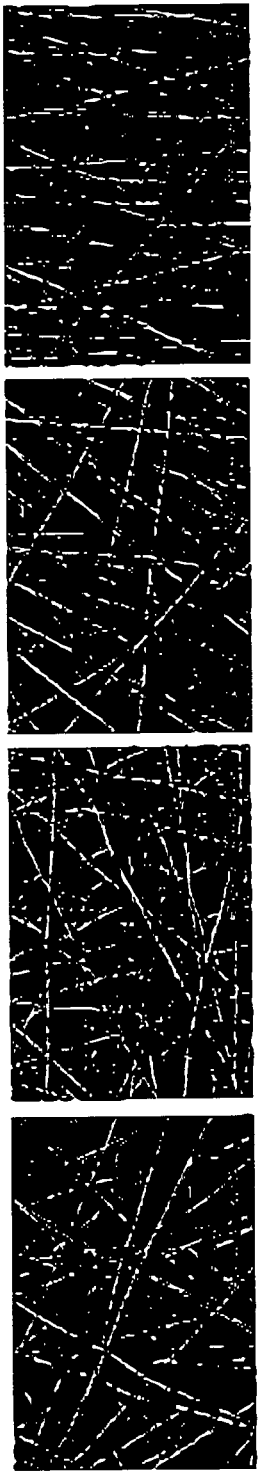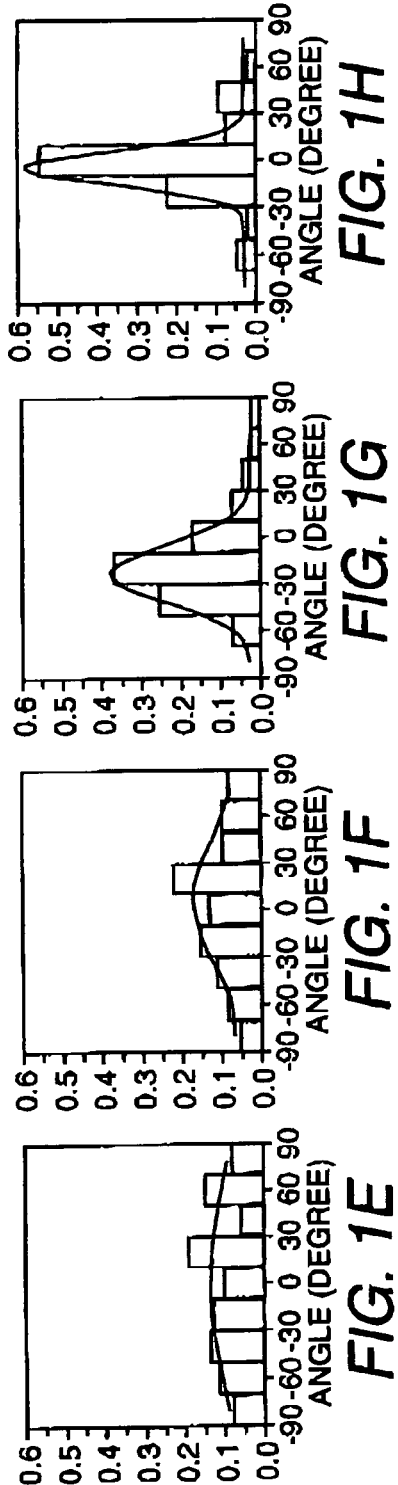

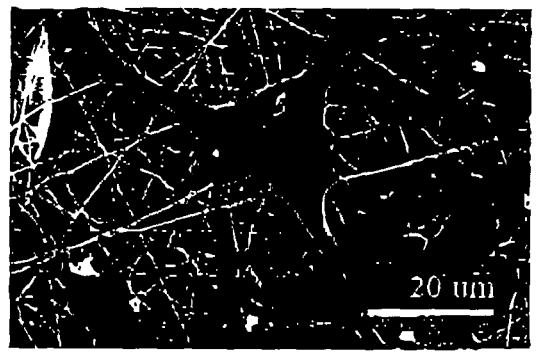
FIG. 5A  FIG. 5B
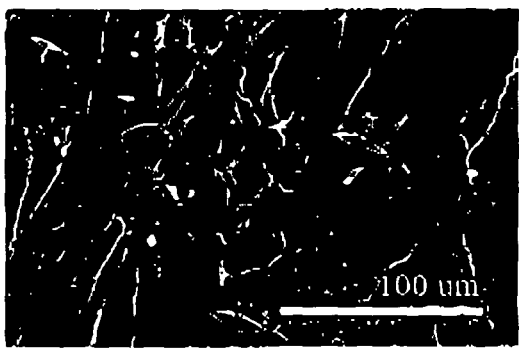
FIG. 5C  FIG. 5D
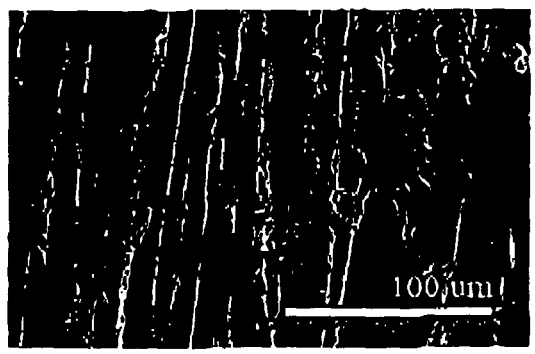
FIG. 5E  FIG. 5F

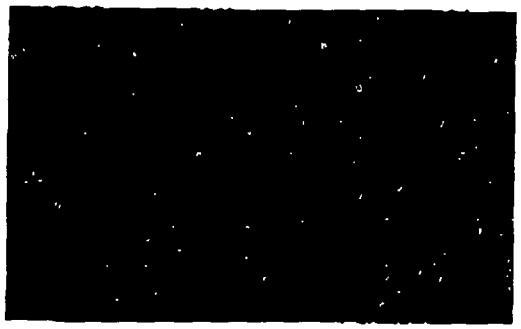
FIG. 6A　　　　　FIG. 6B
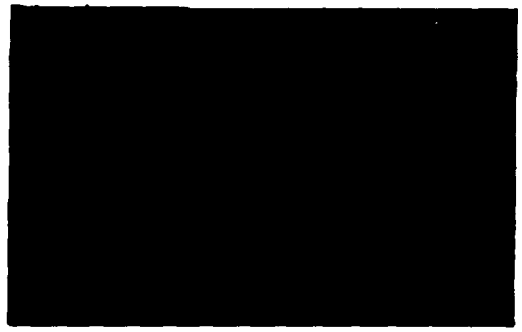
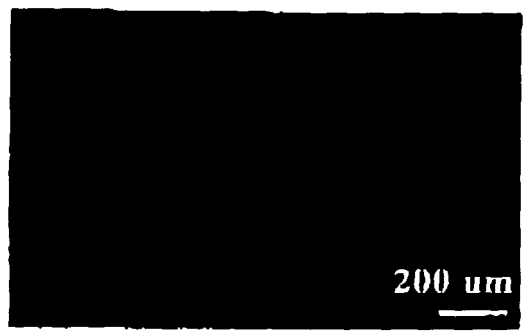
FIG. 6C　　　　　FIG. 6D

 
FIG. 7A   FIG. 7B
 
FIG. 7C   FIG. 7D
 
FIG. 7E   FIG. 7F

ALIGNED SCAFFOLDING SYSTEM FOR SKELETAL MUSCLE REGENERATION

RELATED APPLICATIONS

This application is a 35 U.S.C. §371 national phase application of PCT Application PCT/2009/000625, filed Jan. 30, 2009, and published in English on Aug. 13, 2009, as International Publication No. WO 2009/099570, and which claims the benefit under 35 U.S.C. §119(e) of U.S. Provisional Patent Application Ser. No. 61/025,350, filed Feb. 1, 2008, the disclosure of each of which is incorporated herein by reference in its entirety.

FIELD OF THE INVENTION

The present invention is in the field of tissue engineering, and more particularly, involves the engineering of muscle tissues.

BACKGROUND OF THE INVENTION

Reconstruction of skeletal muscle tissue lost by traumatic injury, tumor ablation, or functional damage due to myopathies is hindered by the lack of available functional muscle tissue substitutes (Bach et al. (2004) Skeletal muscle tissue engineering, *J. Cell Mol. Med.* 8, 413-422). Only a limited degree of functional restoration is provided by muscle transplantation or transposition techniques.

One approach to addressing muscle tissue reconstruction is to engineer a new tissue (Saxena et al. (1999) Skeletal muscle tissue engineering using isolated myoblasts on synthetic biodegradable polymers: preliminary studies, *Tissue Eng* 5, 525-532; Payumo et al. (2002) Tissue engineering skeletal muscle for orthopaedic applications, *Clin. Orthop. Relat Res.* S228-S242; Powell et al. (2002) Mechanical stimulation improves tissue-engineered human skeletal muscle, *Am. J. Physiol Cell Physiol* 283, C1557-C1565). In generating engineered skeletal muscle tissue, it is preferable to mimic native skeletal muscle construction, with its highly-oriented fibers of fused mononucleated muscle cells. The ability to efficiently organize muscle cells to form aligned myotubes in vitro would greatly benefit efforts in skeletal muscle tissue engineering.

SUMMARY OF THE INVENTION

Provided herein are muscle implants including: a biodegradable scaffold comprising a plurality of fibers oriented along a longitudinal axis of the fibers; and mammalian myotubes in said scaffold and oriented along said longitudinal axis of the fibers. Preferably, the implants are anisotropic. In some embodiments, fibers have an average diameter of 100 to 300 nanometers. In some embodiments, fibers include natural polymers (e.g., collagen, elastin, etc.) and/or synthetic polymers (e.g., polycaprolactone (PCL), poly($_{D,L}$-lactide-co-glycolide) (PLGA), polylactide (PLA), and poly(lactide-co-captrolactone) (PLCL)). In some embodiments, natural and synthetic polymers are provided in a ratio of between 2:1 and 1:2 by weight. In some embodiments, myotubes express desmin, myoD and/or myosin heavy chain (MHC). In some embodiments, myotubes have an oriented F-actin structure.

Also provided are methods of forming a biodegradable scaffold, including the steps of: electrospinning a solution comprising a biodegradable scaffold material onto a grounded mandrel to form a plurality of fibers oriented along a longitudinal axis; and crosslinking said fibers to form the scaffold. In some embodiments, fibers include natural polymers (e.g., collagen, elastin, etc.) and/or synthetic polymers (e.g., polycaprolactone (PCL), poly($_{D,L}$-lactide-co-glycolide) (PLGA), polylactide (PLA), and poly(lactide-co-captrolactone) (PLCL)). In some embodiments, natural and synthetic polymers are provided in a ratio of between 2:1 and 1:2 by weight. In some embodiments, the crosslinking step is carried out in the vapor of 2.5% glutaraldehyde solution.

Further provided are methods of forming an anisotropic muscle implant, including the steps of: seeding skeletal muscle cells on a scaffold having oriented fibers; and then forming oriented myotubes from the seeded skeletal muscle cells. In some embodiments, the skeletal muscle cells include myoblasts. In some embodiments, fibers include natural polymers (e.g., collagen, elastin, etc.) and/or synthetic polymers (e.g., polycaprolactone (PCL), poly($_{D,L}$-lactide-co-glycolide) (PLGA), polylactide (PLA), and poly(lactide-co-captrolactone) (PLCL)). In some embodiments, natural and synthetic polymers are provided in a ratio of between 2:1 and 1:2 by weight. In some embodiments, the seeding step is carried out by growing the cells on a scaffold from 0-4 days. In some embodiments, the forming step is carried out by differentiating the cells in a differentiation medium from 1-8 days. In some embodiments, myotubes express desmin and myoD. In some embodiments, myotubes have an oriented F-actin structure.

Methods of treating a subject in need of skeletal muscle reconstruction are provided, including implanting a muscle implant described herein into the subject. In some embodiments, myotubes express desmin, myoD and/or myosin heavy chain (MHC). In some embodiments, myotubes have an oriented F-actin structure.

A further aspect of the present invention is the use of a muscle implant as described herein for the preparation of a device for carrying out a method of treatment for skeletal muscle reconstruction as described herein.

The present invention is explained in greater detail in the drawings and specification set forth below.

BRIEF DESCRIPTION OF THE DRAWINGS

FIG. 1. Fiber angles for the different rates of rotation: (a-d) SEM images of electrospun PCL/collagen nanofibers (×4.0K magnification) and (e-h) normalized histograms of fiber angle, (a, e) static, (b, f) 800 rpm, (c, g) 1500 rpm, and (d, h) 2350 rpm.

FIG. 5. SEM images of human skeletal muscle cells on the electrospun PCL/collagen nanofibers: (a-c) randomly oriented and (d-f) aligned electrospun nanofibers, (a, d) 1 day and (b, e) 3 days after cell seeding and (c, f) 7 days after cell differentiation.

FIG. 6. Immunofluorescent images of F-actin staining in human skeletal muscle cells seeded on the electrospun PCL/collagen nanofibers (×40 magnification): (a, b) 3 days after cell seeding and (c, d) 7 days after differentiation, (a, c) randomly oriented and (b, d) aligned electrospun nanofibers. The cells were aligned along the fiber directions.

FIG. 7. Immunofluorescent staining images of human skeletal muscle cells on the electrospun PCL/collagen nanofibers (×200 magnification): (a-c) randomly oriented and (d-f) aligned electrospun meshes, (a, d) desmin-positive expression at 3 days after cell seeding, (b, e) myosin heavy chain (MHC)-positive expression at 7 days after cell differentiation, and (c, f) sacormeric actin-positive expression at 7 days after cell differentiation.

DETAILED DESCRIPTION OF THE PREFERRED EMBODIMENTS

Figure 2A:
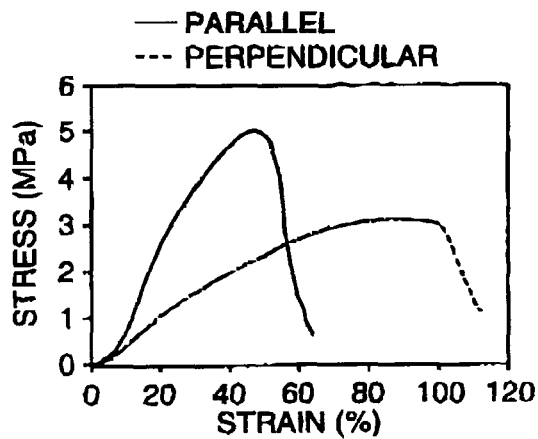
FIG. 2. Mechanical properties of the electrospun PCL/collagen meshes for skeletal muscle regeneration: Stress-strain curves of (a) aligned and (b) random-oriented, (c) ultimate tensile strength and (d) elongation at break.
Figure 2B:
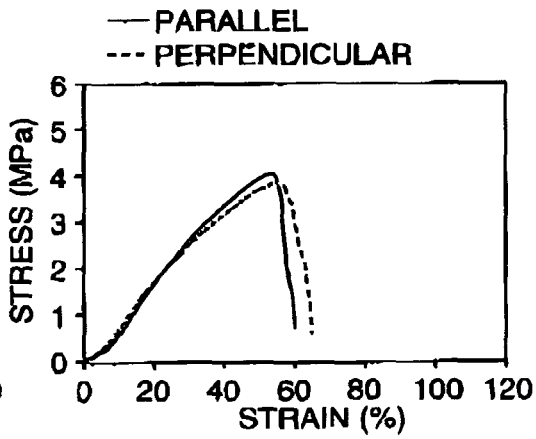
Figure 2C:
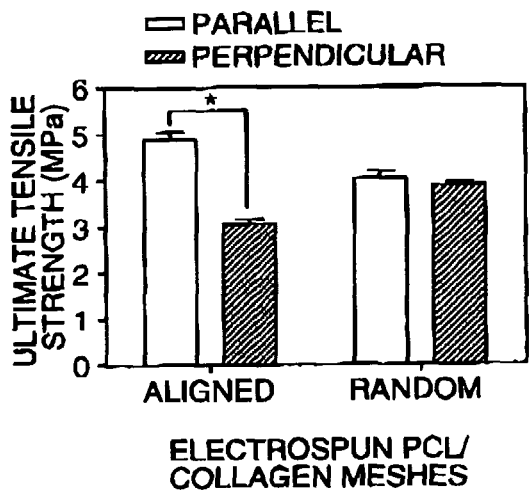
Figure 2D:
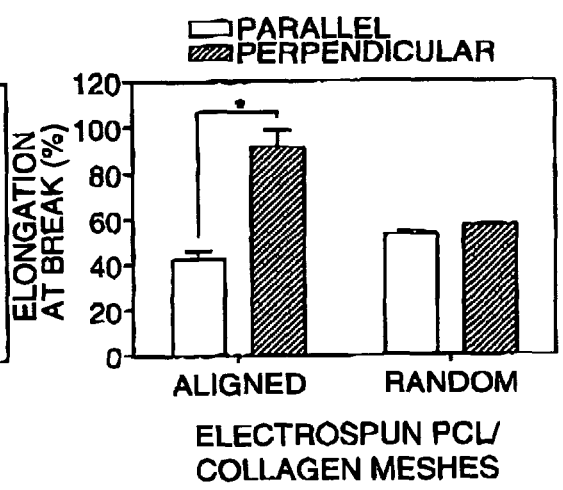

Provided herein and further described below are compositions and methods useful for skeletal muscle regeneration. The disclosures of all United States patent references cited herein are hereby incorporated by reference to the extent they are consistent with the disclosure set forth herein.

As used herein in the description of the invention and the appended claims, the singular forms "a," "an" and "the" are intended to include the plural forms as well, unless the context clearly indicates otherwise. Furthermore, the terms "about" and "approximately" as used herein when referring to a measurable value such as an amount of a compound, dose, time, temperature, and the like, is meant to encompass variations of 20%, 10%, 5%, 1%, 0.5%, or even 0.1% of the specified amount. Also, as used herein, "and/or" or "/" refers to and encompasses any and all possible combinations of one or more of the associated listed items, as well as the lack of combinations when interpreted in the alternative ("or").

"Implant" refers to a product configured to repair, augment or replace (at least a portion of) a natural tissue of a subject (e.g., for veterinary or medical (human) applications). The term "implantable" means the device can be inserted, embedded, grafted or otherwise chronically attached or placed on or in a patient. Implants include, but are not limited to, a scaffold or bioscaffold (which may or may not further comprise cells seeded onto the scaffold or bioscaffold).

"Oriented" cells and/or cell substrates typically have one (or more) axis of orientation (e.g., longitudinal axis), which may be in any desired direction within the region of interest. It will be appreciated that "orienting" as used herein may include partial or total orientation, so long as a sufficient increase in organization is achieved to produce the effect or benefit intended for the particular implementation of the method described herein. For example, fibers and/or cells may be oriented along a longitudinal axis such that greater than 70, 80, 90, or 95% or more of the fibers and/or cells are at an angle of 50, 40, 30, 20, or 10 degrees or less from the reference axis in any direction.

"Anisotropic" means that the physical properties (e.g., elasticity, tensile strength, elongation at break, etc.) of a material (e.g., myotube, scaffold, etc.) are different depending upon the direction of action (e.g., stretch or strain), as opposed to "isotropic," in which the properties of a material are identical in all directions. For example, an anisotropic cell substrate may have a greater ultimate tensile strength along one axis (e.g., the longitudinal axis) than along an axis perpendicular to the axis (e.g., by 0, 1 or 2 to 4, 5, 6 or more MPa). The elongation at break may be smaller along one axis (e.g., the longitudinal axis) than along an axis perpendicular to the axis (e.g., by 10, 20, 30 or 40 to 50, 60, 70 or 80% or more). The peak of a stress curve (MPa) may be reached at a lower strain (%) along one axis (e.g., the longitudinal axis) as compared to an axis perpendicular to the axis. Preferably, the material is tested under wet condition (e.g., immersed in phosphate buffer saline) at room temperature.

"Subjects" are generally human subjects and include, but are not limited to, "patients." The subjects may be male or female and may be of any race or ethnicity, including, but not limited to, Caucasian, African-American, African, Asian, Hispanic, Indian, etc. The subjects may be of any age, including newborn, neonate, infant, child, adolescent, adult and geriatric subjects.

Subjects may also include animal subjects, particularly vertebrate subjects, e.g., mammalian subject such as canines, felines, bovines, caprines, equines, ovines, porcines, rodents (e.g., rats and mice), lagomorphs, non-human primates, etc., or fish or avian subjects, for, e.g., veterinary medicine and/or research or laboratory purposes.

"Treat" refers to any type of treatment that imparts a benefit to a subject, e.g., a patient afflicted with or at risk for developing a disease (e.g., a musculoskeletal disease). Treating includes actions taken and actions refrained from being taken for the purpose of improving the condition of the patient (e.g., the relief of one or more symptoms), delay in the onset or progression of the disease, etc. In some embodiments, treating includes reconstructing skeletal muscle tissue (e.g., where such tissue has been damaged or lost by, e.g., injury or disease) by implanting an anisotropic scaffold (with or without muscle cells) into a subject in need thereof. Scaffolds may be implanted, e.g., at or adjacent to the site of injury, and/or at another site in the body of a subject that would impart a benefit to the subject, as would be appreciated by one of skill in the art.

"Isolated" as used herein signifies that the cells are placed into conditions other than their natural environment. Tissue or cells are "harvested" when initially isolated from a subject, e.g., a primary explant.

"Myoblasts" are a type of muscle stem cell, and are normally closely associated with myofibers during the course of their life cycle in the vertebrate organism. If the myofiber is injured, the myoblasts are capable of dividing and repopulating it. Typically, after muscle injuries myofibers become necrotic and are removed by macrophages (Hurme et al. (1991) Healing of skeletal muscle injury: an ultrastructural and immunohistochemical study, *Med. Sci Sports Exerc.* 23, 801-810). This induces proliferation and fusion of myoblasts to form multinucleated and elongated myotubes, which self-assemble to form a more organized structure, namely muscle fibers (Campion (1984) The muscle satellite cell: a review, *Int. Rev. Cytol.* 87, 225-251).

"Myotubes" are elongated, multinucleated cells, normally formed by the fusion of myoblasts. Myotubes can develop into mature muscle fibers, which have peripherally-located nuclei and myofibrils in their cytoplasm (e.g., in mammals).

Cells may be syngeneic (i.e., genetically identical or closely related, so as to minimize tissue transplant rejection), allogeneic (i.e., from a non-genetically identical member of the same species) or xenogeneic (i.e., from a member of a different species). Syngeneic cells include those that are autogeneic (i.e., from the patient to be treated) and isogeneic (i.e., a genetically identical but different subject, e.g., from an identical twin). Cells may be obtained from, e.g., a donor (either living or cadaveric) or derived from an established cell strain or cell line. For example, cells may be harvested from a donor (e.g., a potential recipient of a bioscaffold graft) using standard biopsy techniques known in the art.

The "primary culture" is the first culture to become established after seeding disaggregated cells or primary explants into a culture vessel. "Expanding" or "expansion" as used herein refers to an increase in number of viable cells. Expanding may be accomplished by, e.g., "growing" the cells through one or more cell cycles, wherein at least a portion of the cells divide to produce additional cells. "Growing" as used herein includes the culture of cells such that the cells remain viable, and may or may not include expansion and/or differentiation of the cells.

"Passaged in vitro" or "passaged" refers to the transfer or subculture of a cell culture to a second culture vessel, usually implying mechanical or enzymatic disaggregation, reseeding, and often division into two or more daughter cultures, depending upon the rate of proliferation. If the population is selected for a particular genotype or phenotype, the culture becomes a "cell strain" upon subculture, i.e., the culture is homogeneous and possesses desirable characteristics (e.g., the ability to express a certain protein or marker).

"Express" or "expression" of a protein or other biological marker means that a gene encoding the same of a precursor thereof is transcribed, and preferably, translated. Typically, according to the present invention, expression of a coding region of a gene will result in production of the encoded polypeptide, such that the cell is "positive" for that protein or other biological marker.

In some embodiments, harvested cells are not passaged. In other embodiments, cells are passaged once, twice, or three times. In still other embodiments, cells are passaged more than 3 times. In some embodiments, cells are passaged 0-1, 0-2 or 0-3 times. In some embodiments, cells are passaged 1-2, 1-3, or 1-4 or more times. In some embodiments, cells are passaged 2-3 or 2-4 or more times. In further embodiments, cells are passaged 5, 8, 10, 12 or 15 or more times. The number of passages used may be selected by, e.g., the relative production of one or more muscle cell proteins and/or markers of interest measured in the cell population after each passage.

"Growth medium" as used herein is a high serum medium that promotes the expansion of cells without or with minimal differentiation. In some embodiments, a skeletal growth medium includes one or more of the following: skeletal muscle basal medium, one or more growth factors (e.g., recombinant human epidermal growth factor (rhEGF)), insulin, gentamicin, amphotericin, fetuin, dexamethasone, bovine serum albumin supplemented with a high amount of serum (e.g., 4.5%-20% fetal bovine serum (FBS)).

"Fusion medium" as used herein is a low serum medium that promotes the differentiation of cells. For cell fusion into multinucleated myotubes, in some embodiments fusion medium includes a minimal medium (e.g., DMEM, EMEM, BME, etc.) containing a low amount of serum (e.g., 0.5-4%).

I. Muscle Cells

Muscle cells include, but are not limited to, muscle fibers or "myocytes," and may be of any suitable species, and in some embodiments are of the same species as the subject into which tissues are implanted. Mammalian cells (including mouse, rat, dog, cat, monkey and human cells) are in some embodiments particularly preferred. Muscle cells include skeletal muscle cells, smooth muscle cells and cardiac muscle cells.

Skeletal muscle cells may be provided by isolating cells from skeletal muscle tissue harvested from the skeletal muscle of an organism, differentiating stem or progenitor cells (e.g., embryonic or amniotic fluid stem cells), etc. Skeletal muscle cells include, but are not limited to, myoblasts, satellite cells and myotubes.

In some embodiments, myoblasts are isolated from muscle tissue by known methods of tissue digestion and grown in vitro. Under high serum conditions, myoblasts continue to proliferate. Under low serum conditions, myoblasts exit the cells cycle and fuse to form multinucleated myotubes, which become contractile. Myoblasts may also form satellite cells, a type of muscle progenitor cells which remain adjacent to myotubes, and can be activated to form myoblasts and differentiate into myotubes.

Skeletal muscle tissue is composed of bundles of highly oriented and dense muscle fibers, each a multinucleated cell derived from a myoblast. The muscle fibers of native tissue are closely packed together in an extracellular matrix to form an organized tissue with high cell density and cellular orientation to generate longitudinal contraction.

In some embodiments, an engineered skeletal muscle tissue includes a scaffold and skeletal muscle cells. Skeletal muscle tissue exhibits significant uniaxial mechanical properties, which are reflective of an extremely oriented underlying extracellular matrix. In some embodiments, the scaffold includes an electrospun nanofiber mesh. In some embodiments, the mesh has a uniaxial fiber angle. In some embodiments, the electrospun meshes are able to promote cellular orientation and fusion and possess uniformly interconnected pores with adequate structural integrity.

II. Cell Scaffolds

"Scaffold" refers to an array of natural or synthetic matrix molecules to which cells or fibers can attach. The fibers may include extracellular matrix molecules or components, such as elastin, elastic strands or peptides, fibrin, collagen, proteoglycans, hyaluronan or hyaluronan oligomers, synthetic fibers or fibrils, or bioactive hydrogels, microparticles, beads, liposomes, or vesicles. Scaffolds may further include extracellular matrix components, such as elastin, elastin-like or elastin-mimetic peptides, fibrin, proteoglycans, commercially available matrix or matrix-substitutes such as Matrigel™ matrix (BD Biosciences, San Jose, Calif., USA), collagen of any type, synthetic fibers or fibrils, or bioactive hydrogels.

A "biodegradable scaffold," "biodegradable mesh" or "biodegradable matrix" is a scaffold having materials capable of being degraded and/or absorbed in a subject's body. Desirably, the scaffold or matrix is porous to allow for cell deposition both on and in the pores of the matrix, and in certain embodiments, is shaped. Such formulations can be prepared by supplying at least one cell population to a biodegradable scaffold to seed the cell population on and/or into the scaffold. In some embodiments, the seeded scaffold is then implanted in the body of the recipient subject, where the organized cell populations facilitate the formation of functional tissue structures.

Biodegradable materials that may be used include, e.g., natural polymers, such as collagen and elastin, and/or synthetic polymers, which can be degraded by hydrolysis at a controlled rate and are reabsorbed. Examples of other suitable materials are provided in U.S. Pat. No. 7,186,554, which is incorporated by reference herein.

Examples of biodegradable synthetic polymers include, but are not limited to, poly(lactide)s, poly(glycolide)s, poly(lactide-co-glycolide)s, poly(lactic acid)s, poly(glycolic acid)s, poly(lactic acid-co-glycolic acid)s, poly(caprolactone)s, polycarbonates, polyesteramides, polyanhydrides, poly(amino acid)s, poly(ortho ester)s, polycyanoacrylates, polyamides, polyacetals, poly(ether ester)s, copolymers of poly(ethylene glycol)s and poly(ortho ester)s, poly(dioxanone)s, poly(alkylene alkylate)s, biodegradable polyurethanes, as well as copolymers thereof. See, e.g., U.S. Pat. No. 7,097,857, which is incorporated by reference herein. Any polymer or copolymer may be combined or blended by methods known in the art.

For example, poly(lactide)s include, but are not limited to, poly(lactide) (also known as polylactic acid, or PLA) such as poly($_L$-lactide) (PLLA), poly($_{D,L}$-lactide) (PDLLA), and copolymers thereof. Copolymers of poly(lactide) include, but are not limited to, poly(lactide-co-glycolide) (PLGA), which is a copolymer of PLA with polyglycolide (PGA) (e.g., poly($_{D,L}$-lactide-co-glycolide)); and poly(lactide-co-caprolactone) (PLCL), which is a copolymer of PLA with poly(caprolactone) (PCL).

Examples of poly(caprolactone)s include, but are not limited to, poly(μ-caprolactone). Copolymers of PCL include, but are not limited to, poly(lactide-co-captrolactone) (PLCL), etc.

The composition of the nanofibers influences the bioresponse (cell-biomaterial interactions) of the cells when seeded on scaffolds. In preferred embodiments, scaffolds comprise a mixture of both natural and synthetic polymers. As an example, a composite scaffolding system including PCL and collagen has been developed that possesses excellent cell compatibility as well as maintains structural integrity (Lee et al. (2008) Development of a composite vascular scaffolding system that withstands physiological vascular conditions, *Biomaterials* 29, 2891-2898). The use of synthetic polymers gives the ability to control scaffold rigidity and degradation rate. In addition, the inclusion of natural polymers can provide biocompatibility and biomimetic environments for cells and tissues.

The interaction of cells with the surfaces of biomaterials is a consideration for understanding cell behaviors such as cell adhesion, proliferation, and migration. It is widely understood that the cell adhesion and proliferation of different types of cells on substrates depends upon the surface characteristics such as wettability, chemistry, electric charge, and topography of surfaces (Lee et al. (1999) Interaction of fibroblasts on polycarbonate membrane surfaces with different micropore sizes and hydrophilicity, *J. Biomater. Sci Polym. Ed* 10, 283-294; Lee et al. (2000) The Effect of Fluid Shear Stress on Endothelial Cell Adhesiveness to Polymer Surfaces with Wettability Gradient, *J. Colloid Interface Sci* 230, 84-90; Lee et al. (2002) Interaction of human chondrocytes and NIH/3T3 fibroblasts on chloric acid-treated biodegradable polymer surfaces, *J. Biomater. Sci Polym. Ed* 13, 197-212; Lee et al. (2003) The effect of surface wettability on induction and growth of neurites from the PC-12 cell on a polymer surface, *J. Colloid Interface Sci* 259, 228-235; Lee et al. (2004) Response of MG63 osteoblast-like cells onto polycarbonate membrane surfaces with different micropore sizes, *Biomaterials* 25, 4699-4707).

Recently, collagen and fibrin biomaterials have been used as a scaffolding system for skeletal muscle regeneration. However, these biomaterials are limited by the tissue size that may be formed. Therefore, in some embodiments, aligned electrospun mesh including a mixture or blend of PCL and/or collagen is combined with primary cultured human skeletal muscle cells for skeletal muscle regeneration. PCL-collagen composite scaffolds according to some embodiments have preferable biomechanical properties, e.g., yield tensile strength, elasticity and compliance. PCL is biodegradable synthetic polymer that supports high mechanical properties, especially, high elongation, but has lower biocompatibility compared to natural polymer such as collagen and elastin. Collagen has a good biocompatibility, but poor mechanical properties and processability. When PCL and collagen are combined together, the mesh can be improved biocompatibility, mechanical properties, and processability. Additionally, in some embodiments the biomechanical properties of PCL-collagen scaffolds are similar to that of native tissue. In some embodiments, skeletal muscle cells readily adhere to the PCL-collagen scaffold, proliferate and fuse into myotubes. In some embodiments, the engineered skeletal muscle has a highly oriented structure and formed anisotropic myotubes.

According to some embodiments, natural and synthetic polymers are provided in a ratio of 1:5, 2:5, 3:5, 4:5, 1:1, 5:4, 5:3, 5:2, 5:1, etc., respectively. Additional natural (e.g., elastin) and/or synthetic (e.g., poly($_{D,L}$-lactide-co-glycolide) (PLGA), poly(lactide) (PLA), poly(lactide-co-captrolactone) (PLCL)) polymers may also be included.

In some embodiments, biodegradable scaffolds are formed by the electrospinning technique. Electrospinning is known in the art and has been used in the fabrication of tissue engineered scaffolds. It is a fiber spinning technique driven by a high voltage electrostatic field using a polymer solution that produces fibers with diameters ranging from several micrometers down to 100 nm or less. In some embodiments, fibers have an average diameter from 10, 100, or 200 nm to 400, 500, 750 or 1000 nm.

The nano-scaled structure of the electrospun scaffolds can support cell adhesion and guide their behavior. Moreover, the composition, structure, and mechanical properties of biomaterials can be controlled (Lee et al. (2007) In vitro evaluation of electrospun nanofiber scaffolds for vascular graft application, *J. Biomed. Mater. Res. A*. in press; Stitzel et al. (2006) Controlled fabrication of a biological vascular substitute, *Biomaterials* 27, 1088-1094). Electrospun nanofiber scaffolds according to some embodiments have a three-dimensional architecture, high porosity with an interconnected pore structure, and a high surface-to-volume ratio, which provides a favorable environment for the cells to grow.

In some embodiments, the biodegradable scaffold can be "shaped" using methods such as, for example, solvent casting, compression molding, filament drawing, meshing, leaching, weaving and coating. In solvent casting, a solution of one or more polymers in an appropriate solvent, such as methylene chloride, is cast as a branching pattern relief structure. After solvent evaporation, a thin film is obtained. In compression molding, a polymer is pressed at pressures up to 30,000 pounds per square inch into an appropriate pattern. Filament drawing involves drawing from the molten polymer and meshing involves forming a mesh by compressing fibers into a felt-like material. In leaching, a solution containing two materials is spread into a shape that resembles the final form. Next, a solvent is used to dissolve away one of the components, resulting in pore formation (see U.S. Pat. No. 5,514,378). In nucleation, thin films in the shape of a reconstructive graft are exposed to radioactive fission products that create tracks of radiation damaged material. Next the polycarbonate sheets are etched with acid or base, turning the tracks of radiation-damaged material into pores. Finally, a laser may be used to shape and burn individual holes through many materials to form a reconstructive graft structure with uniform pore sizes. These shaping techniques may be employed in combination. For example, a biodegradable matrix can be weaved, compression molded and also glued. Furthermore, different polymeric materials shaped by different processes may be joined together to form a composite shape. The composite shape can be a laminar structure. For example, a polymeric matrix can be attached to one or more polymeric matrixes to form a multilayer polymeric matrix structure. The attachment can be performed by gluing with a liquid polymer or by suturing. In addition, the polymeric matrix can be formed as a solid block and shaped by laser or other standard machining techniques to its desired final form. Laser shaping refers to the process of removing materials using a laser.

The biodegradable scaffold can be treated with additives or drugs prior to implantation (before or after it is seeded with cells), e.g., to promote the formation of new tissue after implantation. Thus, for example, growth factors, cytokines, extracellular matrix components, and/or other bioactive materials can be added to the biodegradable scaffold to promote graft healing and the formation of new tissue. Such additives will in generally be selected according to the tissue or organ being reconstructed or augmented, to ensure that appropriate new tissue is formed in the engrafted organ or tissue.

Seeding of cells onto the biodegradable scaffold may be performed according to standard methods. For example, the seeding of cells onto polymeric substrates for use in tissue repair has been reported (see, e.g., U.S. Pat. No. 6,171,344 to Atala, which is incorporated by reference herein; Atala, et al. (1992) *J. Urol.* 148:658-62; Atala, et al. (1993) *J. Urol.* 150:608-12). As an example, cells grown in culture can be trypsinized to separate the cells, and the separated cells can be seeded on the biodegradable scaffold. Alternatively, cells obtained from cell culture can be lifted from a culture plate as a cell layer, and the cell layer can be directly seeded onto the biodegradable scaffold without prior separation of the cells. Cells may also be seeded during formation of the scaffold, e.g., during the electrospinning process (see, e.g., Stankus et al. (2006) Microintegrating smooth muscle cells into a biodegradable, elastomeric fiber matrix. *Biomaterials* 27:735-744).

The density of cells seeded onto the biodegradable scaffold can be varied. For example, in some embodiments greater cell densities promote greater tissue formation by the seeded cells, while lesser densities can permit relatively greater formation of tissue by cells infiltrating the graft from the host. Other seeding techniques can also be used depending on the biodegradable scaffold and the cells. For example, the cells can be applied to the biodegradable scaffold by vacuum filtration. Selection of cell types and seeding cells onto a biodegradable scaffold is routine to one of ordinary skill in the art.

EXAMPLES

It was investigated whether the orientation of electrospun PCL/collagen nanofibers influences the morphology, adhesion, proliferation, differentiation, and organization of human skeletal muscle cells (hSkMCs), and promotes myotube formation.

Fiber orientations were induced by electrospinning onto a collector at different rotation rates. Cell adhesion, proliferation, and differentiation were evaluated from measurements of cell number and phenotypic expression at 1, 3, and 10 days of culture and the diameter, length, and orientation angles of myotube were measured.

I. Materials and Methods

Collagen type I derived from calf skin was purchased from Elastin Products Company (Owensville, Mo., USA). Poly($\mu$-caprolactone) (PCL, Inherent viscosity: 1.77 dL/g in $CHCl_3$ at 30° C.) was obtained from Lactel Absorbable Polymers (Pelham, Ala., USA). 1,1,1,3,3,3-hexafluoro-2-propanol (HFP) and all chemicals were purchased from Sigma Co. (St Louis, Mo., USA) and used as received unless stated otherwise.

Electrospinning.

Electrospun nanofiber meshes were fabricated using a blend of PCL and collagen with a ratio of 1:1 in weight. Both PCL and collagen were dissolved in HFP at a total concentration of 5% (wt/vol). Briefly, the PCL/collagen blend solution was electrospun using a high voltage power supply (Spellman High Voltage, Hauppauge, N.Y., USA) at 20 kV potential between the solution and the grounded surface. The solution was delivered with a 5 mL polypropylene syringe through an 18.5 gauge blunt tip needle at a flow rate of 3.0 mL/hr using a syringe pump (Medfusion 2001, Medex, Inc., Carlsbad, Calif., USA). Fibers were collected onto a grounded mandrel (Custom Design & Fabrication, Richmond, Va., USA) at a distance of 10 cm from the syringe tip. The mandrel, consisting of stainless steel plate (3.8×3.8×0.6 $cm^3$), was rotated at various speeds to achieve different fiber orientations. After the fabrication process, the electrospun PCL/collagen nanofiber meshes were cross-linked under vapor of 2.5% glutaraldehyde solution for 6 hr to increase stability and strength of collagen. The degrees of cross-linking were measured by Ninhydrin assay. All electrospun nanofibers were stored under vacuum for 48 hr to remove residual solvent.

For cell culture studies, the electrospun PCL/collagen nanofiber meshes were placed into 6-well plates, gas sterilized by ethylene oxide (Amsco®Eagle® 3017 EO Sterilizer, Steris Co., Mentor, Ohio, USA) at 30° C. for 36 hr, and incubated at 37° C. for 30 min in culture medium prior to cell seeding.

Characterizations of Electrospun PCL/Collagen Nanofiber Meshes.

Fiber morphologies of the electrospun PCL/collagen nanofiber meshes were examined by scanning electron microscopy (SEM; Model S-2260N, Hitachi Co. Ltd., Japan). Briefly, the electrospun nanofiber meshes were sputter-coated with gold (Hummer™ 6.2, Anatech Ltd, Denver, N.C., USA) to a thickness of 10-15 nm. Images were acquired using an environmental SEM operating at an accelerating voltage of 20 kV with a 10 cm working distance.

The SEM images were analyzed with UTHSCSA ImageTool 3.0 (Freeware provided by the University of Texas Health Sciences Center, San Antonio, Tex., USA) to determine the average fiber diameters and fiber orientations within the nanofiber meshes. The average and standard deviation of fiber diameters were calculated from 60 random measurements per image. In the fiber angles of the nanofibers, histograms were plotted over the entire +90° to −90° range.

Mechanical Testing.

The tensile properties were performed on the electrospun PCL/collagen nanofiber meshes with different fiber orientations in the parallel and perpendicular directions using a uniaxial load testing equipment (Model #5544, Instron Corporation, Issaquah, Wash., USA). A segment of electrospun meshes (10 mm of width, 0.3 mm of thickness, and 30 mm of length) was clamped at its cut ends for the axial testing. The crosshead speed was set at 0.5 mm/sec and the test was stopped when the load decreased by 10% after the onset of failure. This testing was performed under wet condition, immersed in phosphase buffer saline (PBS, pH=7.4), after room temperature incubation for 12 h before tensile testing.

Human Skeletal Muscle Cells.

Human skeletal muscle tissues were taken from biopsies of the rectus abdominalis of male patients undergoing routine surgery (male, age 40-60). Muscle tissues were minced into small pieces and incubated with Dulbecco's Modified Eagle's Medium (DMEM) at 37° C. After 48 hr incubation, enzymatic digestion was performed in collagenase II (0.1% w/v, Worthington Biochemical Co., Lakewood, N.J., USA) and dispase (4 mg/mL, Gibco™, Invitrogen, Carlsbad, Calif., USA) at 37° C. under 5% $CO_2$ for 1 hr in an orbital shaker. The resultant cell pellet was resuspended in medium (DMEM containing 10% horse serum, 1% penicillin/streptomycin) and plated on tissue culture dish. After 2 hr of incubation, unattached cell supernatant was transferred onto a new dish to remove fibroblasts, and this process was repeated two times. Subsequently, the floating cells were plated onto another dish and incubated for 5 days.

Isolated hSkMCs were grown in tissue culture dishes with skeletal muscle growth medium (SkGM-2, Lonza Group Ltd., Basel, Switzerland) containing the basal medium plus recombinant human epidermal growth factor (rhEGF), insulin, gentamicin, amphotericin, fetuin, dexamethasone, and bovine serum albumin supplemented with 5% fetal bovine serum (FBS) until 70% of the cells were confluent. Cell fusion was induced by replacing the growth medium with DMEM/F12 1:1 containing 2% horse serum, 1% penicillin/streptomycin. All reagents for cell culture were purchased from Invitrogen.

The hSkMCs were analyzed for the expression of skeletal muscle specific antigens such as desmin, myoD, and myosin heavy chain (MHC). Briefly, the cultured cells were fixed with cold methanol for 10 min. The samples were incubated for 1 hr in goat polyclonal anti-desmin (1:100), rabbit polyclonal anti-myoD (1:50), and goat polyclonal anti-MHC (1:50) as primary antibodies. All primary antibodies were purchased from Santa Cruz Biotechnology, Inc. (Santa Cruz, Calif., USA). Fluorescein isothiocyanate (FITC) conjugated rabbit anti-goat secondary antibody (1:500, DakoCytomation, Carpinteria, Calif., USA) was used for detection of desmin and MHC and, Texas Red conjugated goat anti-rabbit secondary antibody (1:150) was used for detection of myoD. The samples that were stained without primary antibody served as negative controls. Nuclei were stained using 4'-6-diamidino-2-phenylindole (DAPI).

Fluorescence-activated cell sorter (FACS) analysis was performed for the expression of desmin and myoD. For all antibodies, $5×10^5$ of the cells were incubated in 100 μL of PBS containing 1% FBS and the dilution of primary antibodies ranged from 1:15 to 1:100. The cells were incubated with primary antibody on ice for 30 min, washed with 1% FBS in PBS, re-suspended in 100 μl of FITC-labeled secondary antibody, diluted 1:100 in 1% FBS in PBS, and incubated for an additional 30 min on ice. The cells were washed with PBS containing 1% FBS, and re-suspended in PBS with 1% FBS for FACS analysis. Isotype-matching immunoglobulin (IgG) and FITC-labeled secondary antibody were used to determine nonspecific signals. FACS analyses were measured with a FACS Calibur flow cytometer (BD FACSCalibur System, San Jose, Calif., USA) equipped with an air cooled argon laser (588-nm emission).

Cell Adhesion and Proliferation.

Biological activity of the electrospun PCL/collagen nanofiber meshes was determined by testing the ability of cells to adhere and proliferate. To assess these characteristics, hSkMCs were seeded onto the electrospun meshes. All materials (10×10 $mm^2$) were pre-conditioned with 1×PBS for 30 min and placed in each well of a 24-well culture plate. Cell suspension ($4×10^4$ cells/$cm^2$) was seeded on each sample in growth medium. Adhesion and proliferation of the cells on nanofibers were determined by (3-(4,5-dimethylthazol-2-yl)-5-(3-carbocymethoxyphenyl)-2-(4-sulfophenyl)-2H-tetrazolium, inner salt) (MTS, Promega, Madison, Wis., USA) assay after 1, 3, and 7 days of cell seeding. Briefly, 200 μL of 2 mg/mL MTS solution and 10 μL of 0.92 mg/mL phenazine methosulfate (PMS) were added to each well containing 1.0 ml of fresh medium and incubated at 37° C. and 5% $CO_2$ for 3 hr. The intracellular water-soluble formazan accumulated in the cytoplasm of viable cells was solubilized using culture medium. Absorbance was measured at 490 nm using a microplate reader. Cell proliferation was assessed by the intensity of blue color obtained, which was directly proportional to the metabolic activity of the cell population. The optical density was recorded for quantification (n=5) within the nanofiber meshes.

Cell Seeding on the Electrospun PCL Nanofiber Meshes.

Samples (20×20 $mm^2$) were placed in each well of a 6-well culture plate. Human SkMCs suspension ($4×10^4$ cells/$cm^2$) was seeded on each sample. The cells were grown on the nanofiber meshes in growth medium for 3 days, followed by the formation of myotubes in differentiation medium for 7 days.

To assess cell alignment, hSkMCs seeded on electrospun PCL/collagen nanofiber meshes were examined by SEM. The cell-nanofiber meshes were fixed with 2.5% glutaraldehyde solution at room temperature for 2 hr. The constructs were dehydrated through a series of graded ethanol solutions and then the samples were sputter-coated. Images were acquired using SEM operating at an accelerating voltage of 20 kV with a 10 cm working distance. In addition, microfilaments were stained with rhodamin-phalloidin (Molecular Probes). After staining, the cells were viewed using a Zeiss fluorescence microscope (Carl Zeiss, Inc., Germany).

Immunofluorescent Staining.

hSkMCs seeded on electrospun meshes were detected by using skeletal muscle cell specific antibodies, including anti-desmin, anti-myoD, and anti-MHC. Briefly, the samples were fixed in 4% paraformaldehyde (Polysciences Inc., Warringthon, Pa., USA) for 15 min and washed with PBS 3 times for 5 min each. The cells were permeabilized by incubation with 0.1% Triton-X100 in PBS for 15 min, followed by incubation in 1% BSA in PBS for 20 min to reduce nonspecific background staining. After a gentle rinse in PBS, the samples were incubated for 1 hr in goat polyclonal anti-desmin (1:100), goat polyclonal anti-MHC (1:50), or anti-sarcomeric actin (1:50, Santa Cruz Biotechnology, Inc.) as the primary antibody. The samples were washed with PBS and incubated with the secondary antibody (FITC conjugated rabbit anti-goat, 1:500) for 30 min.

Nuclei were stained using propidium iodide (PI). Samples were visualized using a Zeiss fluorescence microscope.

F-actin assembly was stained by rhodamine-conjugated phalloidin (1:40, Molecular Probes) incubation for 1 hr. Nuclei were stained with Yo-Pro®-1 (1:100, Molecular Probes). The images were recorded using a laser scanning confocal microscopy (Olympus TCS-SL, Center Valley, Pa., USA). The confocal images represent 2-D projections of 3-D stacked images.

Analyses of the Orientation, Diameter, and Length of Myotubes on Electrospun Nanofiber Meshes.

For measuring the alignment, diameter, and length of myotubes, immunofluorescent images of anti-MHC staining were analyzed under 40 and 200 magnifications and measured by ImageTool 3.0 software. For myotube orientation, the value of 0° denoted parallel alignment from the axis of the nanofiber and 90° represented perpendicular alignment.

Statistical Analysis.

The differences between the randomly oriented and aligned electrospun PCL/collagen nanofiber meshes for analyses of tensile properties, measurement of diameters and length of myotubes were evaluated by Student's t-test. Data from the cell adhesion and proliferation were analyzed using ANOVA. Differences were considered significant if P<0.05.

II. Results

Fabrication and Characterization of the Electrospun PCL/Collagen Nanofiber Meshes.

PCL/collagen blend solution was electrospun onto the stainless steel plate at different rotation speeds to form various fiber orientations in the nanofibers. SEM images of the resulting fibers showed nano-scaled fiber diameters and controlled fiber orientations (FIG. 1a). The electrospun meshes of the PCL/collagen blend were produced from solutions having a total polymer concentration ranging from 3% to 10% (wt/vol) in HFP. The electrospun meshes showed a linear relationship between solution concentrations and fiber diameters (data not shown). We had recently found that the optimal fabrication condition based on the fiber diameters was a 5% (wt/vol) solution concentration (see Lee et al. (2007) Development of a composite vascular scaffolding system that withstands physiological vascular conditions, *Biomaterials* 29, 2891-2898). Homogeneous fibers with average diameters of approximately 300 nm were obtained from a solution concentration of 5% (wt/vol). The rotation speed of the mandrel did not influence the nanofiber diameter (Table 1).

TABLE 1

Average fiber diameter of electrospun PCL/collagen nanofibers with different rotation rate

| Rotation rate (rpm) | Fiber diameter (nm) |
|---|---|
| Static | 334 ± 125 |
| 800 | 297 ± 67 |
| 1000 | 275 ± 102 |
| 1500 | 306 ± 111 |
| 2350 | 281 ± 68 |
| 3480 | 296 ± 97 |

PCL/collagen nanofiber meshes with different fiber angles were produced by electrospinning at various rotation rates of 0 (static), 800, 1500, and 2350 rpm. Progressive increase in fiber orientation was observed as the rotation rate increased (FIG. 1b). Histograms for orientation of electrospun meshes indicate a close correlation between fiber distribution (bars) and the wrapped normal distribution function (curve).

Tensile Testing.

Fiber alignment had a profound effect on the mechanical properties of electrospun PCL/collagen nanofiber meshes. In FIG. 2, the ultimate tensile strength of the aligned nanofiber meshes showed significant differences between parallel (4.9±0.2 MPa) and perpendicular (3.1±0.1 MPa) directions (P<0.05). However, the randomly oriented nanofiber meshes did not show significant differences. The results of the elongation at break of the meshes showed a similar pattern.

Human Skeletal Muscle Cells.

Figure 3A:
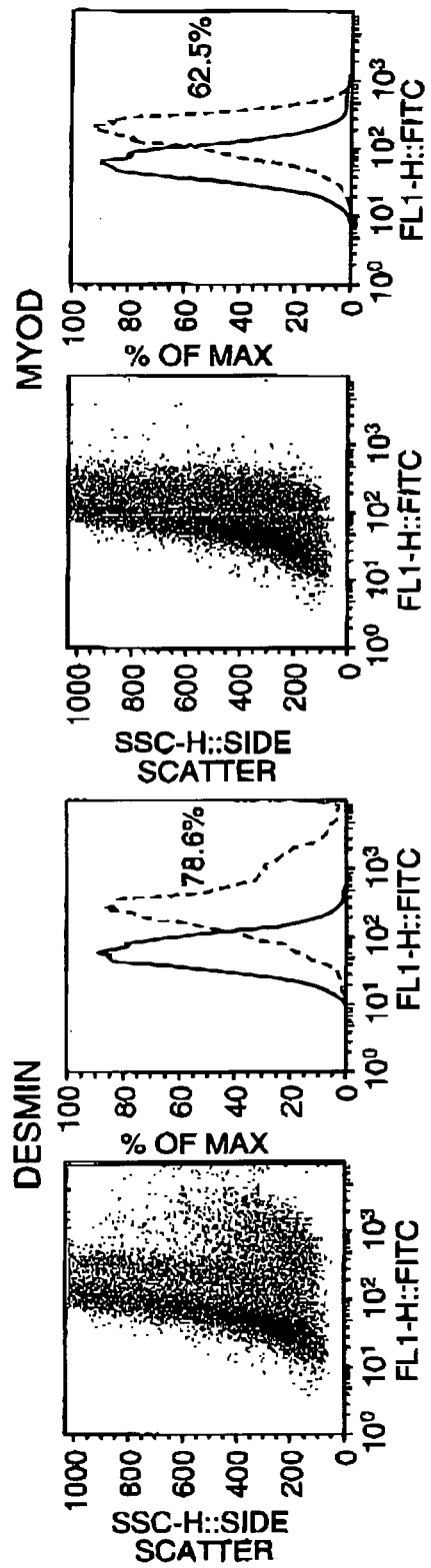
FIG. 3. Human skeletal muscle in monolayer cultures: (a) FACS analyses for desmin and MyoD and (b) immunofluorescent staining for desmin, MyoD, and myosin heavy chain (MHC). At passage 5, human skeletal muscle cells highly expressed desmin (78.6%) and MyoD (62.5%). The cells were fused in differentiation medium and formed myotubes expressing MHC after 7 days of differentiation.
Figure 3B:

Human SkMCs were isolated successfully from patient samples. Under high serum conditions, the skeletal muscle cells continued to proliferate. When placed under low serum conditions, the cells fused to form multinucleated myotubes. FACS analysis of the cells at passage 5 confirmed the results of immunocytochemical staining for the expression of desmin, myoD, and MHC (FIG. 3). Cells at all passages examined showed a strong and consistent expression of desmin (78.6% at passage 5) and myoD (62.5% at passage 5), indicating a skeletal muscle cell phenotype. The cells fused and formed myotubes that expressed MHC in the fusion medium after 7 days (FIG. 3b).

Cell Adhesion and Proliferation.

Figure 4:
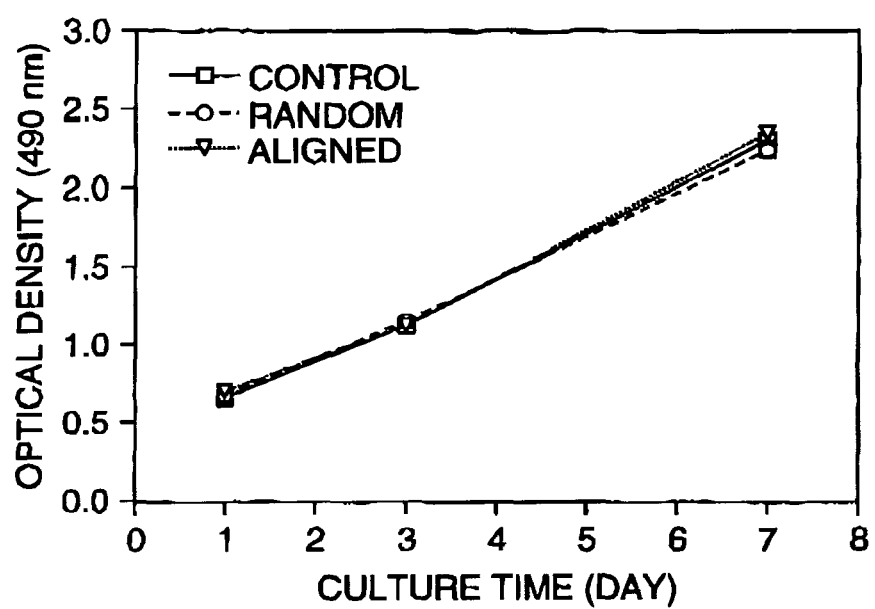
FIG. 4. Human skeletal muscle cell adhesion and proliferation on the electrospun PCL/collagen nanofibers with different fiber orientation as measured by MTS assay. Tissue culture dishes served as a control. There was no difference in the cell adhesion and proliferation between each group.
Figure 8A:
FIG. 8. Laser confocal microscopy images of F-actin staining in human skeletal muscle cells seeded on the electrospun PCL/collagen nanofibers (×600 magnification): (a, b) 3 days after cell seeding and (c, d) 7 days after cell differentiation; (a, c) randomly oriented and (b, d) aligned electrospun nanofibers (green: nuclei, red: F-actin).
Figure 8B:
Figure 8C:
Figure 8D:

To evaluate cell adhesion and proliferation on the electrospun PCL/collagen nanofiber meshes, hSkMCs were seeded on the nanofiber meshes. The muscle cells readily adhered and proliferated for up to 7 days in culture, indicating that the nanofiber meshes were conducive to cell adhesion and proliferation. Cells grown on tissue culture dishes served as controls. In this experiment, cell adhesion and proliferation on the electrospun meshes did not show significant differences between the control, randomly oriented, and aligned nanofiber meshes (FIG. 4).

Cell Morphology.

SEM images showed the presence of hSkMCs on the electrospun PCL/collagen nanofiber meshes at 1 and 3 days after cell seeding and 7 days after cell differentiation (FIG. 5). The cells were aligned on the unidirectionally oriented nanofibers after cell seeding. In contrast, the randomly oriented nanofiber meshes induced an irregular cellular orientation. The hSkMCs formed myotubes on the electrospun nanofibers at 7 days after cell differentiation. The myotubes that formed on the oriented nanofiber meshes showed unidirectionally organized myotubes that are consistently aligned along the longitudinal axis of nanofibers, which is in contrast to the randomly oriented nanofiber meshes (FIGS. 5c, f).

Immunofluorescent images of the F-actin staining of the hSkMCs on electrospun meshes showed the evidence of cell alignment at 3 days after cell seeding and myotube formation at 7 days after cell differentiation (FIG. 6). Cell alignment showed that the F-actin fibers were oriented along the longitudinal axis of the nanofiber direction. On the randomly oriented nanofiber meshes, myotubes were mostly scattered in a wide range of directions (FIG. 6c). The myotubes formed on the randomly oriented nanofiber meshes showed partial alignment locally and did not show a global cellular organization. In contrast, myotubes on the aligned nanofiber meshes organized within close proximity to the direction of the nanofiber direction and formed globally aligned myotubes (FIG. 6d).

Immunofluorescent Staining.

Phenotypic expression of desmin, MHC, and sarcomeric actin were confirmed on the aligned and randomly oriented nanofiber meshes at 3 days after cell seeding and myotube formation at 7 days after cell differentiation (FIG. 7). Both the aligned and randomly oriented nanofiber meshes showed the maintenance of phenotypic expression of the skeletal muscle cells.

Confocal microscopic images confirmed that fiber orientation influenced the morphology and cytoskeleton of hSkMCs on the nanofiber meshes (FIG. 8). Confocal microscopy of fluorescent stained F-actin on cell adhesion, proliferation, and differentiation demonstrated that the actin assembly appeared disordered on the randomly oriented nanofiber structure. In contrast, on the aligned nanofiber structures, the F-actin was oriented along the nanofiber direction in an organized fashion.

Myotube Orientation, Diameter, and Length.

Figure 9A:
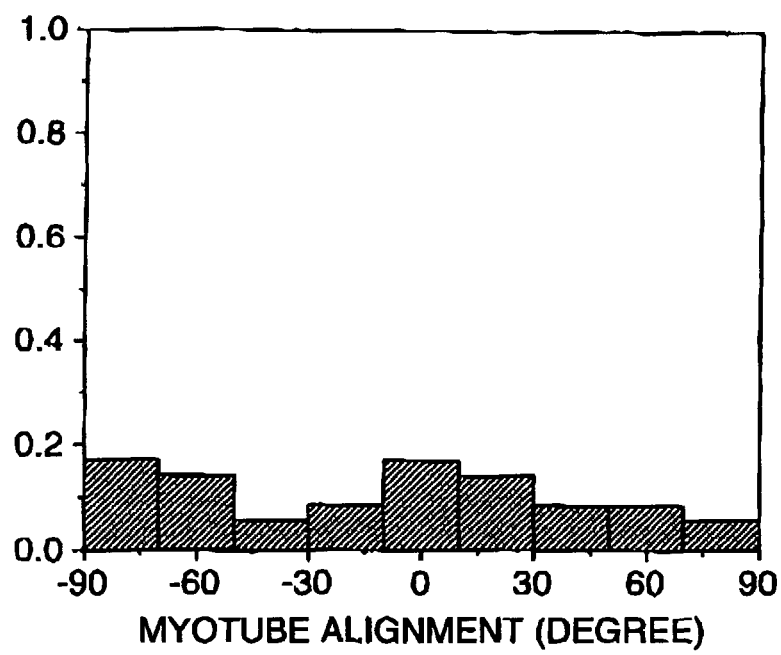
FIG. 9. Myotube alignment on (a) randomly oriented and (b) aligned electrospun PCL/collagen nanofiber meshes at 7 days after cell differentiation.
Figure 9B:
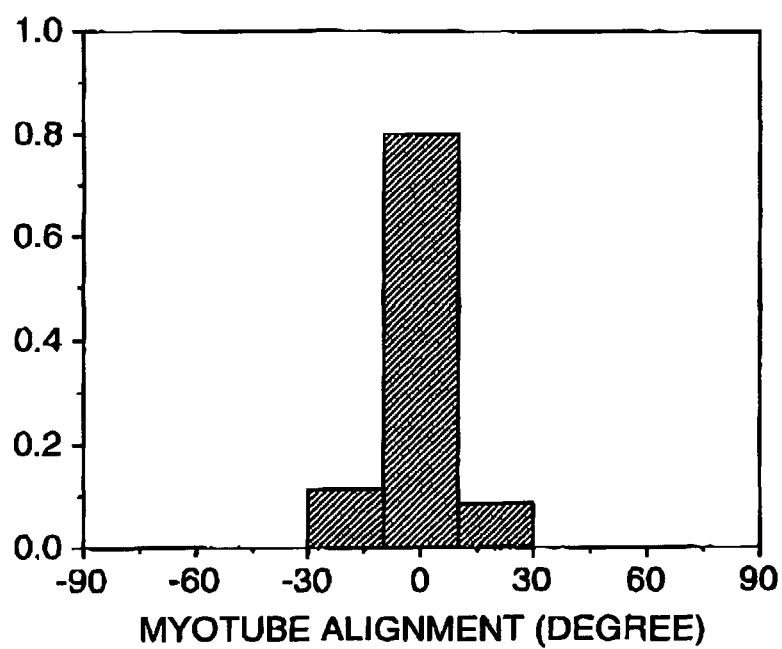

To quantify the effects of aligned nanofiber meshes on hSkMCs fused into myotubes, the angle, diameter, and length of myotubes were measured by using immunofluorescent images. The minimum myotube alignment value of 0° denoted parallel alignment from the axis of the nanofiber meshes and the maximum of 90° represented perpendicular alignment. The aligned nanofiber meshes promoted skeletal muscle morphogenesis into parallel-oriented myotubes (FIG. 9). On the aligned nanofiber meshes, the myotubes were highly organized.

Figure 10A:
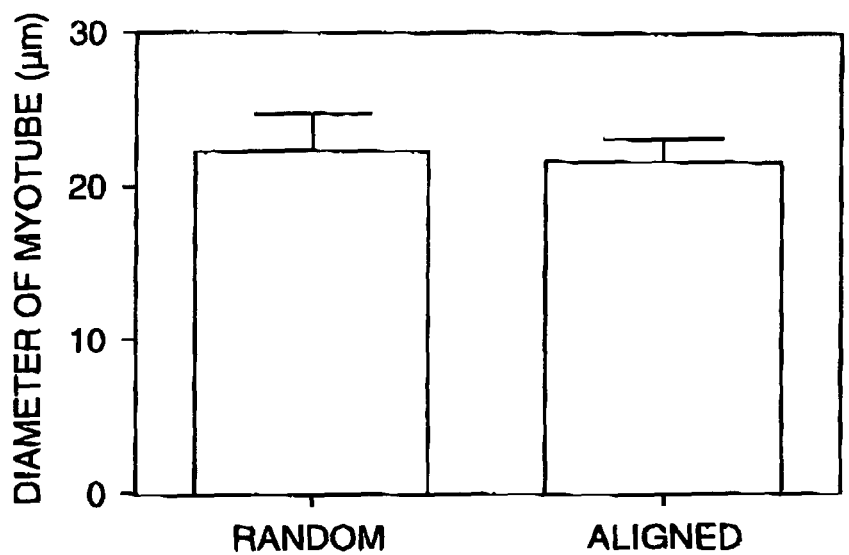
FIG. 10. Human skeletal muscle cell morphology at 7 days after cell differentiation; (a) diameter and (b) length of myotubes.
Figure 10B:
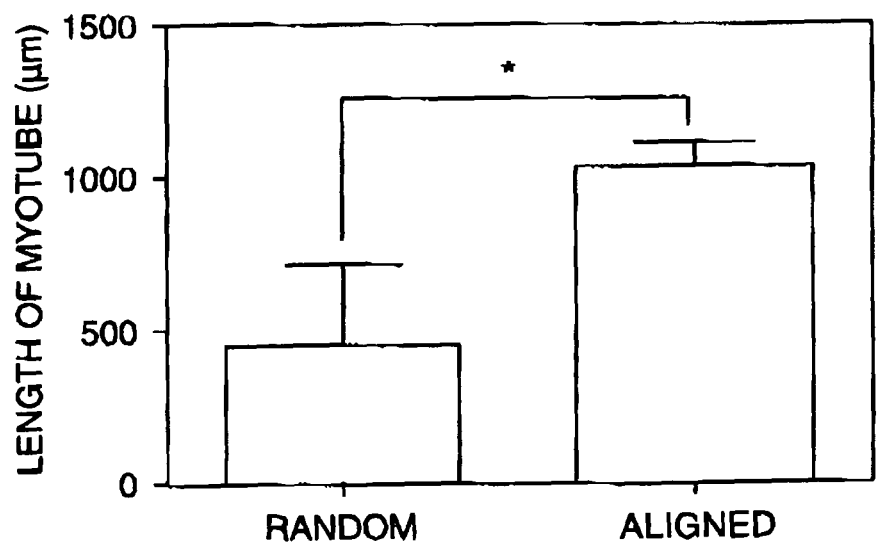

The diameter of myotubes was not significantly different between the aligned and randomly oriented nanofiber mesh groups (FIG. 10a). However, the length of myotubes on the aligned nanofiber meshes was more than twice the length of the myotubes on the randomly oriented meshes ($P<0.05$), which support the hypothesis that aligned nanofibers promote myotube formation (FIG. 10b).

III. Discussion

Skeletal muscle tissue consists of bundles of unidirectionally oriented muscle fibers that consist of multinucleated cells. These fibers are closely packed together in three dimensional ECM proteins to form an organized tissue with cellular orientation to generate longitudinal contraction (Bach et al. (2004) Skeletal muscle tissue engineering, *J. Cell Mol. Med.* 8, 413-422). To closely mimic the skeletal muscle architecture, this study was designed to fabricate nanofiber meshes that are aligned in a unidirectional manner to facilitate myotube formation. Cell adhesion, proliferation, and differentiation of hSkMCs were evaluated on the electrospun nanofiber meshes with different fiber orientations. It is shown that oriented nanofiber meshes, composed of PCL and type I collagen, can be fabricated using electrospinning technology. hSKMCs are able to adhere, grow and fuse into myotubes along the longitudinal axis of nanofibers.

Electrospinning technology offers many advantages, including the production of nano-scaled fibers with spatial orientation, high aspect ratio, high surface area, and controlled pore geometry, depending on target configurations. Some of these parameters can be optimized to enhance cellular growth and function in vitro and in vivo, leading to improved cell adhesion, cellular expression, and diffusion of oxygen and nutrients (Li et al. (2002) Electrospun nanofibrous structure: a novel scaffold for tissue engineering, *J. Biomed. Mater. Res.* 60, 613-621). In addition, nanofibers fabricated by the electrospinning method can be axially aligned by using an appropriate collecting mandrel. Previous studies show that aligned nanofibrous structures can be obtained using a variety of collecting mandrel systems, including rotating drum (Bashur et al. (2006) Effect of fiber diameter and orientation on fibroblast morphology and proliferation on electrospun poly(D,L-lactic-co-glycolic acid) meshes, *Biomaterials* 27, 5681-5688), parallel electrodes (Li et al. (2003) Electrospinning of polymeric and ceramic nanofibers as uniaxially aligned arrays, *Nano Letters* 3, 1167-1171), rotating wire drum (Katta et al. (2004) Continuous electrospinning of aligned polymer nanofibers onto a wire drum collector, *Nano Letters* 4, 2215-2218), and disc collector (Theron et al. (2001) Electrostatic field-assisted alignment of electrospun nanofibres, *Nanotechnology* 12, 384-390). In this study the rotating drum system was used due to its simplicity and the feasibility of producing large meshes. A range of rotation speeds of the mandrel was examined up to 3480 rpm. Levels of fiber alignment improved with an increase in the rotation rate.

The composition of the nanofibers is important because it influences the bioresponse of the cells when seeded onto scaffolds (Song et al. (2007) Bioactive and degradable hybridized nanofibers of gelatin-siloxane for bone regeneration, *J. Biomed. Mater. Res. A*). This composite scaffolding system hybridizing natural and synthetic polymers possesses excellent bioreactivity as well as maintains structural integrity (Lee et al. (2007) Development of a composite vascular scaffolding system that withstands physiological vascular conditions, *Biomaterials* 29, 2891-2898). The use of a synthetic scaffold as a base material has several advantages, including the ability to control scaffold rigidity and degradation rate. In addition, naturally derived substances are able to provide the required biocompatibility and biomimetic environment for cells and tissues.

The composite scaffold fabricated for skeletal muscle tissue engineering possessed these favorable characteristics. The PCL/collagen composite scaffolds showed excellent biomechanical properties, including the yield tensile strength, elasticity, burst pressure strength, and compliance. In this study hSkMCs were successfully isolated from muscle biopsies and tested for purity, phenotypic and functional expression. The cells readily adhered and proliferated on all nanofiber meshes, and fused into myotubes. Moreover, the cells were able to maintain their phenotypic and functional expression on the scaffolds. The purity of hSkMCs was also maintained throughout the study. These results indicate that the nanofibers fabricated from PCL/collagen may be an ideal scaffold for skeletal muscle tissue engineering.

There are many factors that can guide cellular growth and orientation. This study examined whether organized nanofibrous scaffolds would permit self-alignment of the skeletal muscle cells, as muscle tissue function is dictated by the structure and organization of muscle fibers (Wakelam (1985) The fusion of myoblasts, *Biochem. J.* 228, 1-12). Aligned nanofibers greatly influenced muscle cell organization and enhanced myotube formation. The myotubes formed on the aligned nanofiber meshes were highly organized and were significantly longer than that of the myotubes on the randomly oriented meshes. These findings indicate that the electrospun PCL/collagen nanofiber meshes are able to guide and orient skeletal muscle cells into organized structures that mimic native tissues. The aligned composite nanofiber scaffolds seeded with skeletal muscle cells provides implantable functional muscle tissues for patients with large muscle defects.

IV. Conclusions

PCL/collagen nanofiber meshes fabricated by electrospinning show a unidirectional fiber orientation that can guide hSKMCs alignment and enhance myotube formation. The electrospun meshes are biocompatible, biodegradable, easily fabricated, and are able to support cell adhesion, proliferation, and differentiation. Aligned PCL/collagen nanofibers facilitate skeletal muscle cell organization.

The foregoing is illustrative of the present invention, and is not to be construed as limiting thereof. The invention is defined by the following claims, with equivalents of the claims to be included therein.

That which is claimed is:

1. An anisotropic muscle implant comprising:
   (a) a biodegradable scaffold comprising a plurality of fibers oriented along a longitudinal axis, wherein said fibers comprise:
      (i) a natural polymer; and
      (ii) a synthetic polymer,
      wherein said natural polymer and said synthetic polymer are in a ratio of between 2:1 and 1:2 by weight; and
   (b) mammalian myotubes in said scaffold and oriented along said longitudinal axis of said fibers,
   wherein said scaffold has an ultimate tensile strength along said longitudinal axis that is between 1 and 6 MPa greater than an ultimate tensile strength along an axis perpendicular to said longitudinal axis, measured with a crosshead speed of 0.5 millimeters per second at room temperature under wet condition.

2. The implant of claim 1, wherein said plurality of fibers is oriented along said longitudinal axis such that 70% or more of the fibers are at an angle of 50 degrees or less from said longitudinal axis.

3. The implant of claim 1, wherein said myotubes are oriented along said longitudinal axis such that 70% or more of the fibers are at an angle of 50 degrees or less from said longitudinal axis.

4. The implant of claim 1, wherein said fibers have an average diameter of between 100 and 1000 nanometers.

5. The implant of claim 1, wherein said natural polymer is selected from the group consisting of collagen and elastin; and said synthetic polymer is selected from the group consisting of polycaprolactone (PCL), poly($_{D,L}$-lactide-co-glycolide) (PLGA), polylactide (PLA), poly(lactide-co-captrolactone) (PLCL), and combinations thereof.

6. The implant of claim 1, wherein said fibers comprise collagen and polycaprolactone (PCL).

7. The implant of claim 1, wherein said myotubes express desmin, myoD and myosin heavy chain (MHC).

8. The implant of claim 1, wherein said myotubes comprise an oriented F-actin structure.

9. A method of forming a biodegradable scaffold, comprising:
   electrospinning a solution comprising a biodegradable scaffold material onto a grounded mandrel to form a plurality of fibers oriented along a longitudinal axis, said fibers comprising a natural polymer and a synthetic polymer, wherein said natural polymer and said synthetic polymer are in a ratio of between 2:1 and 1:2 by weight; and
   crosslinking said fibers to form said scaffold,
   wherein said scaffold has an ultimate tensile strength along said longitudinal axis that is between 1 and 6 MPa greater than an ultimate tensile strength along an axis perpendicular to said longitudinal axis, measured with a crosshead speed of 0.5 millimeters per second at room temperature under wet condition.

10. The method of claim 9, wherein said natural polymer is selected from the group consisting of collagen and elastin; and said synthetic polymer is selected from the group consisting of polycaprolactone (PCL), poly($_{D,L}$-lactide-co-glycolide) (PLGA), polylactide (PLA), poly(lactide-co-captrolactone) (PLCL), and combinations thereof.

11. The method of claim 9, wherein said fibers comprise collagen and polycaprolactone (PCL).

12. The method of claim 9, wherein said crosslinking step is carried out in a vapor of 2.5% glutaraldehyde solution.

13. A method of forming an anisotropic muscle implant comprising:
   providing skeletal muscle cells;
   seeding said skeletal muscle cells on a scaffold comprising oriented fibers, wherein said fibers comprise:
      (i) a natural polymer; and
      (ii) a synthetic polymer,
      wherein said natural polymer and said synthetic polymer are in a ratio of between 2:1 and 1:2 by weight, said seeding comprising growing said cells on said scaffold in a growth medium; and then
   forming oriented myotubes from said skeletal muscle cells, said forming comprising differentiating said skeletal muscle cells that have been seeded onto said scaffold in a fusion medium, thereby forming said anisotropic muscle implant,
   wherein said scaffold has an ultimate tensile strength along said longitudinal axis that is between 1 and 6 MPa greater than an ultimate tensile strength along an axis perpendicular to said longitudinal axis, measured with a crosshead speed of 0.5 millimeters per second at room temperature under wet condition.

14. The method of claim 13, wherein said skeletal muscle cells comprise myoblasts.

15. The method of claim 13, wherein said natural polymer is selected from the group consisting of collagen and elastin; and said synthetic polymer is selected from the group consisting of polycaprolactone (PCL), poly($_{D,L}$-lactide-co-glycolide) (PLGA), polylactide (PLA), poly(lactide-co-captrolactone) (PLCL), and combinations thereof.

16. The method of claim 13, wherein said fibers comprise collagen and polycaprolactone (PCL).

17. The method of claim 13, wherein said seeding step is carried out by growing said cells on said scaffold from 0-4 days.

18. The method of claim 13, wherein said forming step is carried out by differentiating said cells in a differentiation medium from 1-8 days.

19. The method of claim 13, wherein said myotubes express desmin and myoD.

20. The method of claim 13, wherein said myotubes comprise an oriented F-actin structure.

21. A method of treating a subject in need of skeletal muscle reconstruction comprising implanting the anisotropic muscle implant of claim 1 into said subject.

22. The implant of claim 1, wherein said fibers have an average diameter of between 200 and 750 nanometers.

23. The implant of claim 1, wherein said natural polymer and said synthetic polymer are in a ratio of 1:1 by weight.

24. The method of claim 9, wherein said fibers have an average diameter of between 200 and 750 nanometers.

25. The method of claim 9, wherein said natural polymer and said synthetic polymer are in a ratio of 1:1 by weight.

26. The method of claim 13, wherein said fibers have an average diameter of between 200 and 750 nanometers.

27. The method of claim 13, wherein said natural polymer and said synthetic polymer are in a ratio of 1:1 by weight.

* * * * *